United States Patent [19]

Donzis

[11] 4,370,754

[45] * Feb. 1, 1983

[54] VARIABLE PRESSURE PAD

[75] Inventor: Byron A. Donzis, Houston, Tex.

[73] Assignee: American Pneumatics Co., Houston, Tex.

[21] Appl. No.: 80,095

[22] Filed: Sep. 28, 1979

Related U.S. Application Data

[63] Continuation-in-part of Ser. No. 928,425, Jul. 27, 1978, Pat. No. 4,217,705, which is a continuation-in-part of Ser. No. 842,250, Oct. 14, 1977, abandoned, which is a continuation-in-part of Ser. No. 774,276, Mar. 4, 1977, abandoned.

[51] Int. Cl.³ .......................................... A41D 13/00
[52] U.S. Cl. ................................................. 2/2; 2/16; 2/22; 2/DIG. 3; 2/413
[58] Field of Search ...................... 2/2, 2.5, 16, 20, 22, 2/24, 413, DIG. 3

[56] References Cited

U.S. PATENT DOCUMENTS

| | | | |
|---|---|---|---|
| 1,229,947 | 6/1917 | Haggerty | 2/2 |
| 1,657,866 | 1/1928 | Mooney | 2/2 |
| 1,726,939 | 9/1929 | Anderson | 2/2 X |
| 1,915,754 | 6/1933 | O'Shea | 2/2 |
| 1,991,721 | 2/1935 | Becket et al. | 2/2 |
| 2,247,961 | 7/1941 | Mulvey | 2/2 |
| 2,266,886 | 12/1941 | McCoy | 2/2 |
| 3,366,970 | 2/1968 | Morgan | 2/2 |
| 3,500,472 | 3/1970 | Castellani | 2/2 |
| 3,514,784 | 6/1970 | McDavid | 2/2 |
| 3,550,159 | 12/1970 | Alarco | 2/2 |
| 3,866,241 | 2/1975 | Grant | 2/2 |
| 3,921,222 | 11/1975 | Hollman | 2/2 |
| 3,945,041 | 3/1976 | Rhee | 2/2 |
| 3,995,320 | 12/1976 | Zafuto | 2/2 |
| 4,084,264 | 4/1978 | Marion | 2/2 |
| 4,089,065 | 5/1978 | McGee | 2/2 |

Primary Examiner—H. Hampton Hunter
Attorney, Agent, or Firm—Murray Robinson; Ned L. Conley; David A. Rose

[57] ABSTRACT

The protective garment of the present invention primarily for use as protective athletic equipment includes protective gear for the shoulders, ribs, biceps, forearms, thighs, knees and shins. The protective garment is generally composed of variable pressure pads, air cushions, and/or shields. The variable pressure pad includes two superimposed plies of a light-weight, non-elastic fluid-impervious fabric material having the adjacent surfaces of the material sealed around the periphery to form a pressure tight inflatable garment which does not distend and other adjacent surfaces sealed at regions internally of the periphery to define a plurality of fluid chambers and fluid passageways. The internal fluid chambers are fluidly communicable with adjacent fluid chambers by means of the fluid passageways. The material crinkles and folds over at preselected regions to constrict fluid communication between the fluid chambers as an external force is applied to the variable pressure pads. Air cushions in the form of a plurality of tubular air chambers are mounted on the variable pressure pads at certain critical locations to provide additional cushioning and dispersion of an external force over an area wider than the impact area. Shields are mounted over the variable pressure pads and/or air cushions to provide additional means for apportioning the external force. Vent holes are provided in the variable pressure pads and shields to permit the garment to breathe by permitting air to pass from the surface of the body and through the pads creating a chimney effect beneath the variable pressure pads.

32 Claims, 18 Drawing Figures

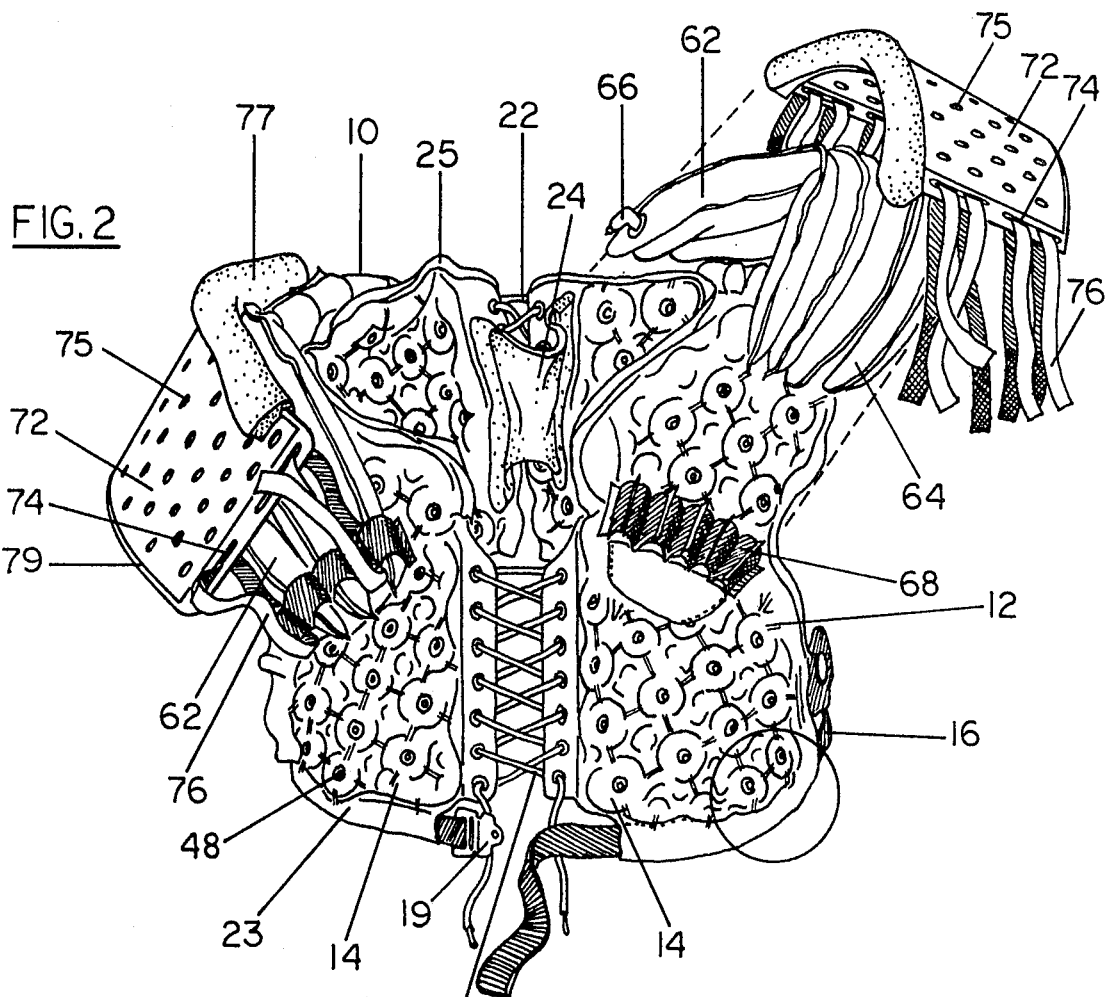
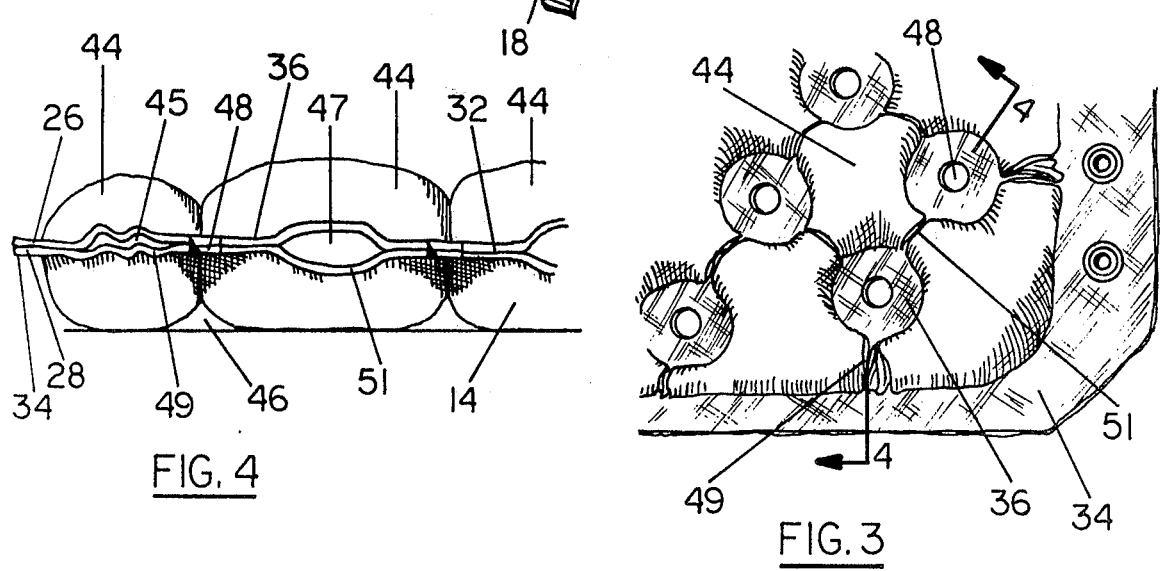

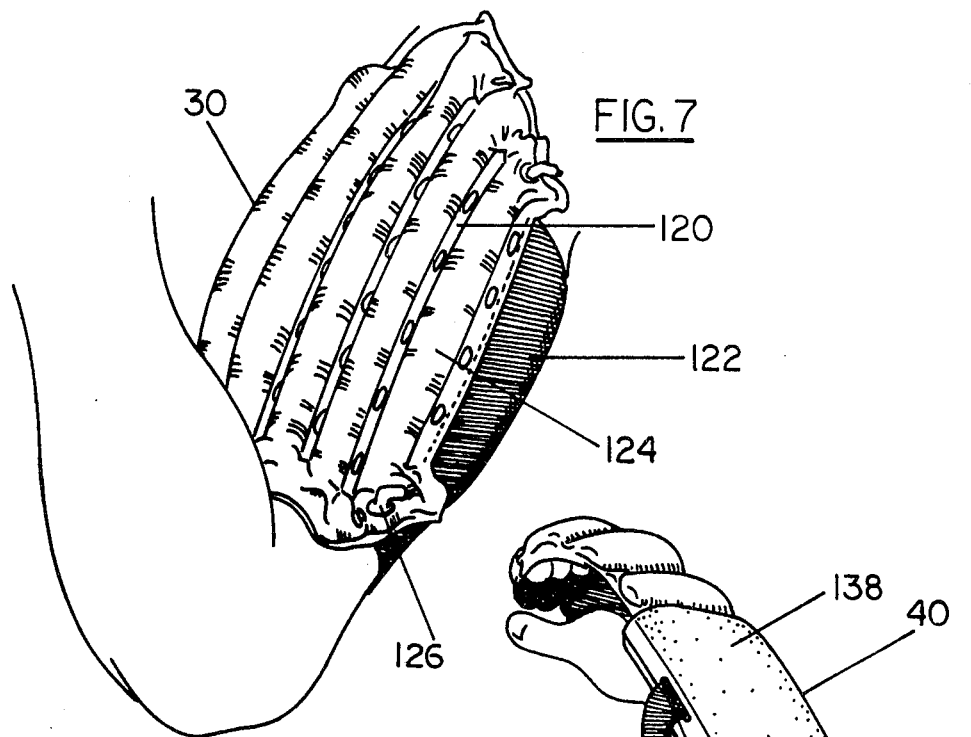
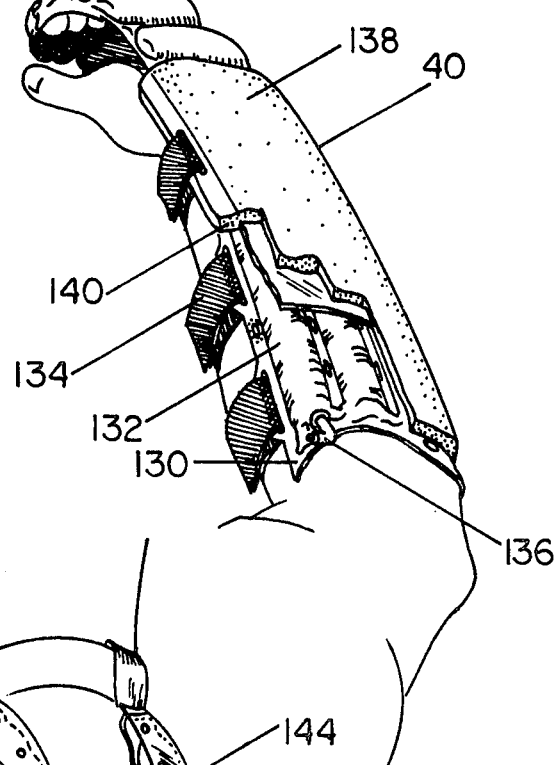
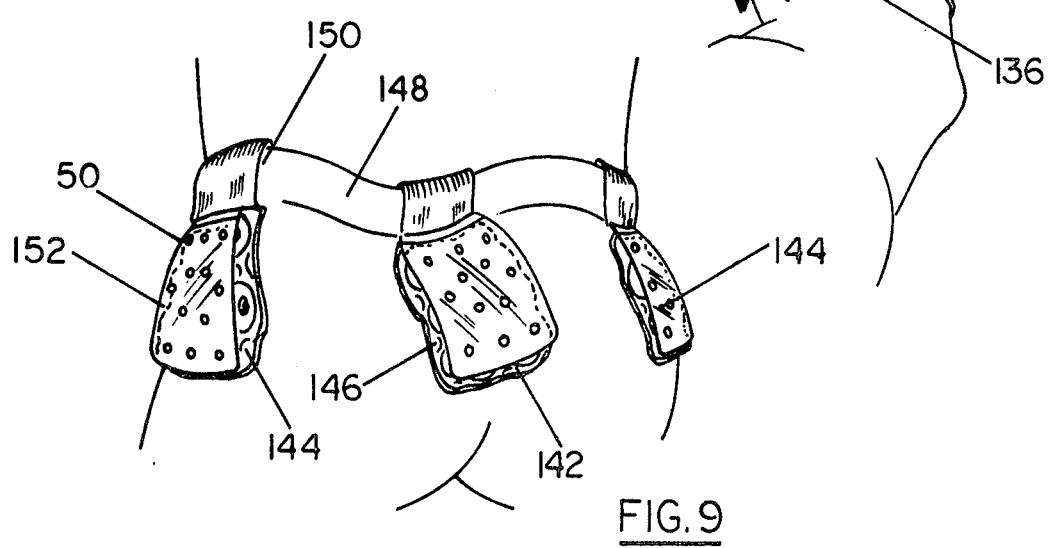

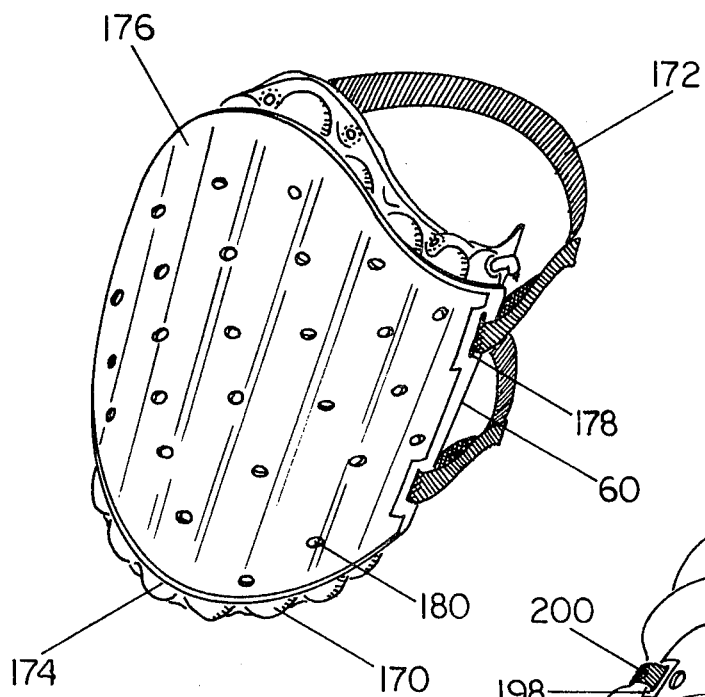
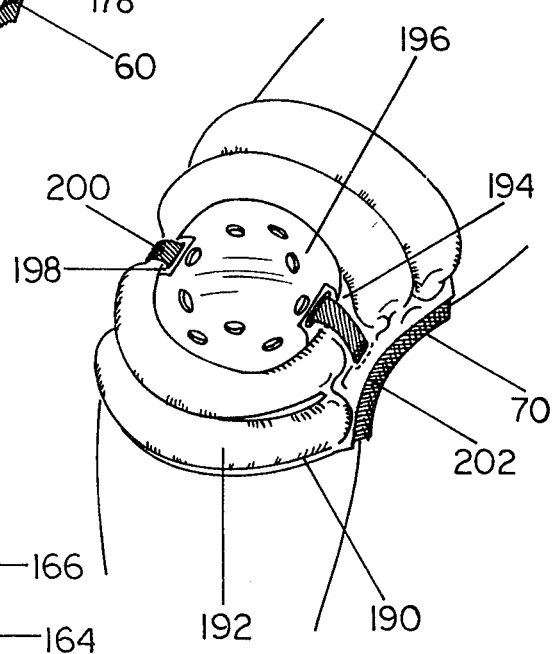
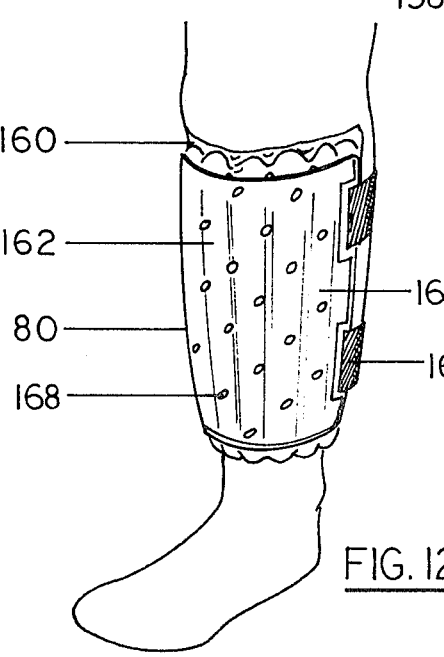

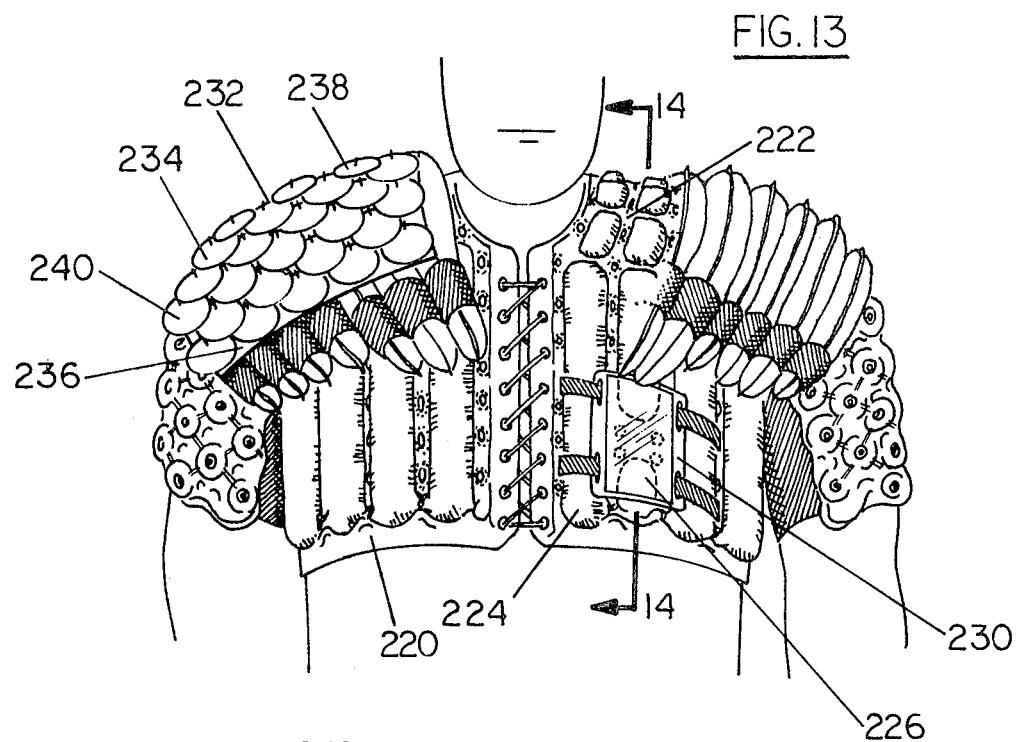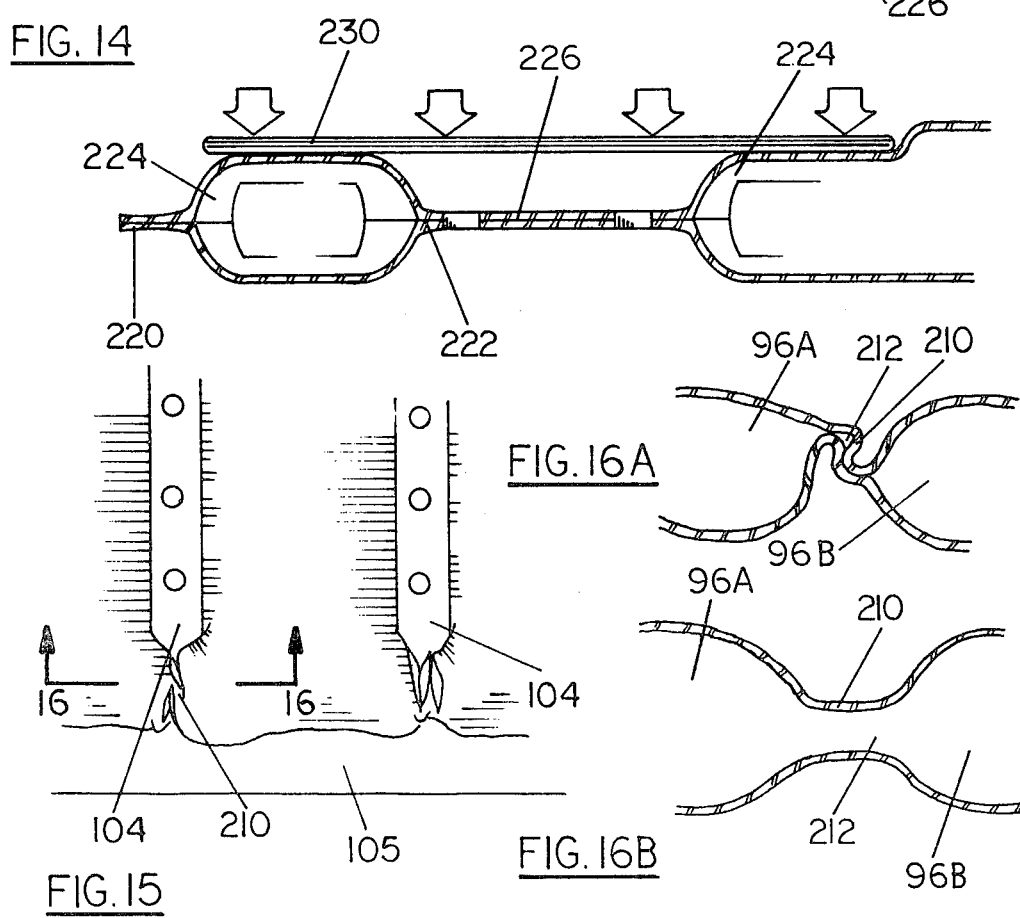

VARIABLE PRESSURE PAD

REFERENCE TO RELATED APPLICATIONS

This application is a continuation-in-part of U.S. Application Ser. No. 928,425, filed July 27, 1978, and now U.S. Pat. No. 4,217,705, dated Aug. 19, 1980 which in turn is a continuation-in-part of U.S. Application Ser. No. 842,250, filed Oct. 14, 1977, and now abandoned, which in turn was a continuation-in-part of U.S. Application Ser. No. 774,276, filed Mar. 4, 1977, and now abandoned.

TECHNICAL FIELD

This invention relates to protective garments and more particularly to protective athletic equipment worn by athletes participating in body contact sports such as football, hockey, baseball, motocross, Karate, skiing, sky diving, etc. It should be understood, however, that although the equipment of the present invention has been designed specifically for use by athletes, the basic concept is applicable to other garments worn to protect the body for preventing injuries, for avoiding the aggravation of previously incurred injuries, and for providing body insulation.

BACKGROUND OF THE ART

Contact sports since their early days have caused injuries to the players. Many such sports permit heavy body contact resulting in very dangerous injuries. Although protective equipment is constantly being improved in design, often such protective items have not been effective in preventing injuries. Injuries continue to be serious, frequently cause disabilities, and occasionally are fatal.

The primary goal of protective equipment is to protect the wearer against injury or against aggravation of a previous injury. It is desirable for a player to play his full potential without fear of injury or without fear of magnifying an existing injury. Further, such equipment must be designed so as not to inflict injury upon another player.

Many athletic committees have been formed to establish rules governing equipment specifications and banning dangerous equipment items. Since players, especially in football and hockey, are required to use their hands, arms, and legs to push or block the opposition, protective equipment is encouraged to prevent arm and leg bruises but regulated to prevent such equipment from being used as weapons against an opposing player. Thus various football committees have expressly forbidden the use of any hard or unyielding materials on a player's elbow, forearm, wrist or hand because of the danger of injury to other players unless proper padding is used.

Injuries result mainly from collision with opposing players or with the ground after forceful contact with another player. Often the agent of injury is the hard protective equipment such as the helmet, shoulder pads, and arm, thigh or knee guards worn by the player. The hard striking surface of such protective gear can bring devastating injury if it hits an unprotected area with sufficient force.

Sports have been marred for spectators where key players are injured and miss several games due to the injury. With the limiting of rosters and increased player salaries, it is important to limit injuries and to provide protection to existing injuries permitting the early return of the injured player to the game.

Prior athletic protective gear emphasizes the use of hard coverings over resilient slow recovery foam padding. Shoulder pads, for example, include a shield which rides on some type of a pad mounted on the shoulder and the shield has to ride above the pad to absorb sufficient shock. Therefore, the shield sticks up so as not to conform to the contour of the body and operates in a highly mechanized fashion. Such designs are bulky, heavy, uncomfortable, and expensive and are not effective in distributing blows over a larger area to reduce their effect.

Prior art athletic equipment is rebuilt and reconditioned every year, and if it becomes damaged, it is time consuming and expensive to repair. Further such equipment is not hygienic since the padding absorbs perspiration and cannot be washed regularly. The equipment requires huge locker areas to dry and store.

Such equipment has the further disadvantage of being fixed in design and cannot be adapted to the individual player's needs. Therefore consideration in uniform design cannot be given to the position played by the individual, his size and agility, any prior injuries, and any particularly vulnerable body locations.

A wide variety of pneumatic devices has been proposed and tested over the years in an attempt to improve protective athletic equipment. These devices typically include an inflatable cushion used with some other item of protective equipment. Often these devices have sealed air chambers which merely transfer the shock to the body. Such valveless devices cannot vary the pressure between the air chambers.

In prior art devices incorporating any degree of fluid flow between two or more chambers, communication between chambers is typically by means of passageways and/or valves located in the middle of the inflatable device. Such prior devices tend to lose pressure and, as a result, it is inevitable that a "bottoming out" will occur blocking off fluid passage between the chambers and destroying the functional valve of such passageways. When mechanical valving is involved, a loss of internal pressure causes the body to engage the valve, clearly an undesirable situation.

Other prior art pneumatic equipment is made of elastomeric material permitting the pneumatic pad to "balloon" out of shape upon receiving a blow. Such ballooning permits "bottoming out" thereby destroying the principal function of the equipment, i.e. to protect the body from receiving the blow. To date no pneumatic protective device has achieved widespread acceptance or use.

The present invention overcomes the deficiencies of previous equipment by providing a substantially improved pneumatic protective garment. It provides an improved protective guard which complies with equipment regulations, is easy to wear, reduces the weight and bulkiness of prior equipment, is hygienic, is structurally simple and is relatively inexpensive to manufacture. Further, the present invention provides a unique valving to prevent "bottoming out", does not "balloon" out of shape, conforms to the body contour, and is adaptable to the player's needs.

DISCLOSURE OF THE INVENTION

The protective garment of the present invention primarily for use as protective athletic equipment includes protective gear for the shoulders, ribs, biceps, forearms, thighs, knees, and shins. The protective garment is generally composed of variable pressure pads, air cushions, and/or shields. The variable pressure pad includes two superimposed plies of a lightweight, non-elastic fluid-impervious fabric material having the adjacent surfaces of the material sealed around the periphery to form a pressure tight inflatable garment which does not distend and other adjacent surfaces sealed at regions internally of the periphery to define a plurality of fluid chambers and fluid passageways. The internal fluid chambers are fluidly communicable with adjacent fluid chambers by means of the fluid passageways. The material crinkles and folds over at preselected regions to constrict fluid communication between the fluid chambers as an external force is applied to the variable pressure pads. Thus the material provides a natural valving and serves as a baffle to fluid flow between chambers. Air cushions in the form of a plurality of tubular air chambers are mounted on the variable pressure pads at certain critical locations to provide additional cushioning and dispersion of an external force over an area wider than the impact area. Shields are mounted over the variable pressure pads and/or air cushions to provide additional means for apportioning the external force. Vent holes are provided in the variable pressure pads and shields to permit the garment to breathe by permitting air to pass from the surface of the body and through the pads creating a chimney effect beneath the variable pressure pad.

BRIEF DESCRIPTION OF THE DRAWINGS

For a detailed description of a preferred embodiment of the invention, reference will now be made to the accompanying drawings wherein:

FIG. 2 is a perspective view of the front of the shoulder pad with a portion thereof shown in an exploded view;

FIG. 3 is a plan view of the circled portion of the shoulder pad shown in FIG. 2;

FIG. 4 is a sectional view of the portion of the shoulder pad of FIG. 2 shown in FIG. 3, taken along line 4—4;

FIG. 7 is a perspective view of the bicep pads;

FIG. 8 is a perspective view of the forearm pads;

FIG. 9 is a perspective view of the hip pads;

FIG. 10 is a perspective view of the front of the thigh pads;

FIG. 11 is a perspective view of the front of the knee pads;

FIG. 12 is a perspective view of the front of the shin pads;

FIG. 13 is a front view of an alternative embodiment of the shoulder pads for a defensive player having a fish scale shield and a tubular variable pressure pad;

FIG. 14 is a sectional view of the shoulder pad of FIG. 13, taken at line 14—14.

FIG. 15 is a plan view of the circled portion of the rib pad shown in FIG. 6;

FIG. 16A is a sectional view of the portion of the rib pads of FIG. 2, shown in FIG. 15 taken at line 16—16 and FIG. 16B is the sectional view of FIG. 16A upon the rib pads receiving an external force.

DESCRIPTION OF THE PREFERRED EMBODIMENT

The protective garment of the present invention finds particular utility in several areas and design emphasis shifts depending upon the demands on the garment due to the application. For example, the garment may be used as athletic equipment to protect players, as a cushioning device for the military, as a protective pad for medical patients, as an insulative garment, and as a safety cushion for vehicles, among other uses. Each application requires a predetermined design based on the application. Therefore, it should be understood that although the preferred embodiment described below is for athletic apparel used in connection with the more violent sports such as football, the present invention has application in other areas as described herein.

Figure 1:
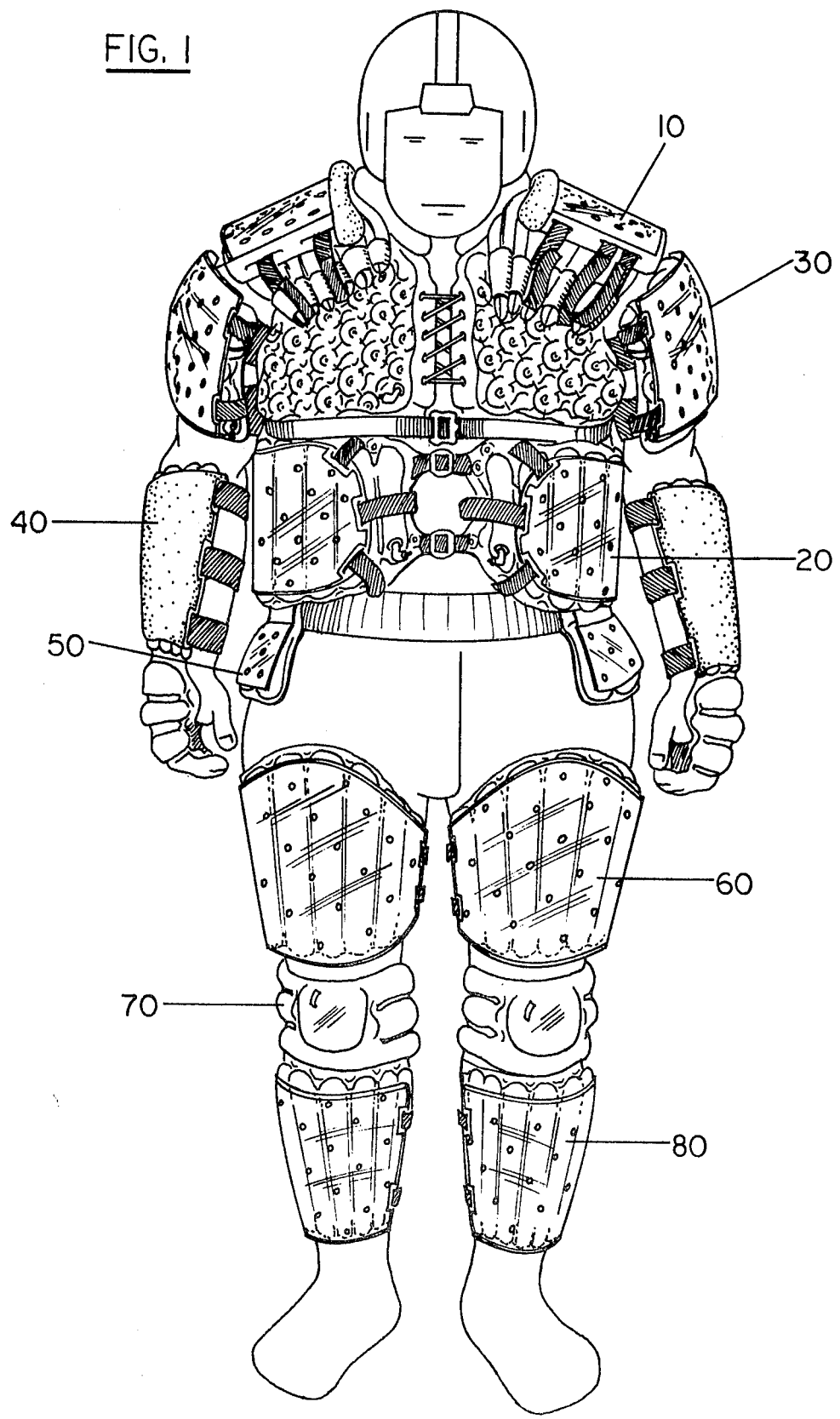
FIG. 1 is an elevation view of the protective football uniform.

Referring initially to FIG. 1, the protective athletic garment of the present invention includes: shoulder pads 10, rib pads 20, bicep pads 30, forearm pads 40, hip pads 50, thigh pads 60, knee pads 70, and shin pads 80. The invention may also be adapted to pad other parts of the body such as padding in a football helmet to protect the head. The pads have three general parts, a variable pressure pad, an air cushion, and a shield. Each pad making up the uniform includes a variable pressure pad and may include an air cushion and/or shield at the physician's or trainer's option permitting the uniform to be customized to meet the needs of the individual player and to adapt it to the position that he plays.

Referring now to FIG. 2 illustrating shoulder pads 10, pads 10 have an undergarment 12 comprised of two variable pressure pads 14, one for the left side and one for the right side. Each variable pressure pad 14 extends from the upper torso in front, over a shoulder, to the upper torso of the back. the front and back portions of left and right variable pressure pads 14 are connected under the arms by straps 16, and left and right variable pressure pads 14 are connected to each other by eyelets and lace 18 and belt 19 in front and by eyelets and lace 22 in the back. Right and left variable pressure pads 14 may be attached together by any appropriate attachment means such as Velcro, laces, clasps, snaps, zippers or eyelets and lace. Any tightening means well known to the art may be used and it will be understood that any equivalent fastening means of which various pads may be fixed together will be acceptable. A cloth band 23 is affixed to the lower edge of undergarment 12 and may be a continuation of straps 16 and/or belt 19. A fabric 25 is sewn onto the remaining periphery of undergarment 12. Flaps 24 may be provided between the underside and top of the undergarment 12 to avoid exposure of the fastening means to the body which might cause irritation.

Referring now to FIGS. 3 and 4, variable pressure pad 14 comprises two superimposed plies 26, 28 of thin, lightweight, non-elastic, flexible, fluid-impervious woven fabric material of a shape generally conforming to the shape of each side of the upper torso of the body. The adjacent surfaces of plies 26, 28 are sealed at 32 around the periphery 34 of pad 14 and at preselected regions 36 internally of periphery 34 to form a pressure type inflatable variable pressure pad which, when filled with fluid under sufficient pressure to adequately cushion the applied forces, does not distend or lose its shape. Pad 14 may be pressurized with any suitable fluid, preferably air but possibly another gaseous or liquid fluid.

The fabric material for inflated pad 14 must have sufficient strength to be integral and self-supporting, while at the same time be lightweight and flexible. The pad of the present invention must be capable of retaining and supporting its own shape under the limited amount of internal fluid pressure to which it will be subjected during proper functioning. In other words, it must not stretch or "balloon" out of shape when cushioning or when subjected to sudden and sharp increases in internal pressure as will be experienced during an athletic event. In addition, it must be capable of supporting its own structure without being contained by some rigid supporting material. This last characteristic provides pad 14 with the valuable capability of being made to a precise shape.

The preferred material for the manufacture of variable pressure pad 14 is a woven fabric of a suitably strong, non-elastic fiber, such as nylon, polyester, or aramid, made fluid-impervious by coating it on at least one side with a natural or synthetic elastomeric material, such as rubber, polyisoprene, or polyurethane. Other suitably strong, fiber materials which may be square woven into a textile sheet material which is non-elastic and of sufficient strength to resist puncture and the like will be obvious to those having ordinary skill in the art. Also, although not preferred, hydrophilic fibers such as cotton, linen and the like may be utilized, in which case it would be preferable to thoroughly impregnate the fabric by coating it on both sides with elastomeric material, for example. As always, the critical criteria for suitability will be the weight of the material and its strength and resistance to "ballooning". Prior art materials, such as natural rubber do not hold their shape. Other materials, such as polyvinylcholoride (pvc) or the like, lose their flexibility and become too heavy when used in a thickness adequate to prevent "ballooning" under pressure The opposing plies 26, 28 of the fabric material may be adhered to each other by any suitable technique, including the use of adhesive, the only criterion being that an effective seal be formed. Such sealing may be accomplished using a cement adapted for bonding the particular rubber material used in coataccording to established techniques (including the use of RF radio signals). Heat sealing provides for flexibility and adaptability in manufacturing, which is important in producing a predetermined pattern and/or design in the size, shape, number and arrangement of preselected regions 36 for individual use. Heat sealing is well known in the art. As will be apparent, whatever sealing technique is employed, the resulting seal must be adequate to withstand the internal pressure control when pad 14 is inflated, but more importantly, when inflated pad 14 is subjected to the external forces of anticipated use. These forces will tend to compress pad 14, drastically increasing the internal pressure.

Figure 5:
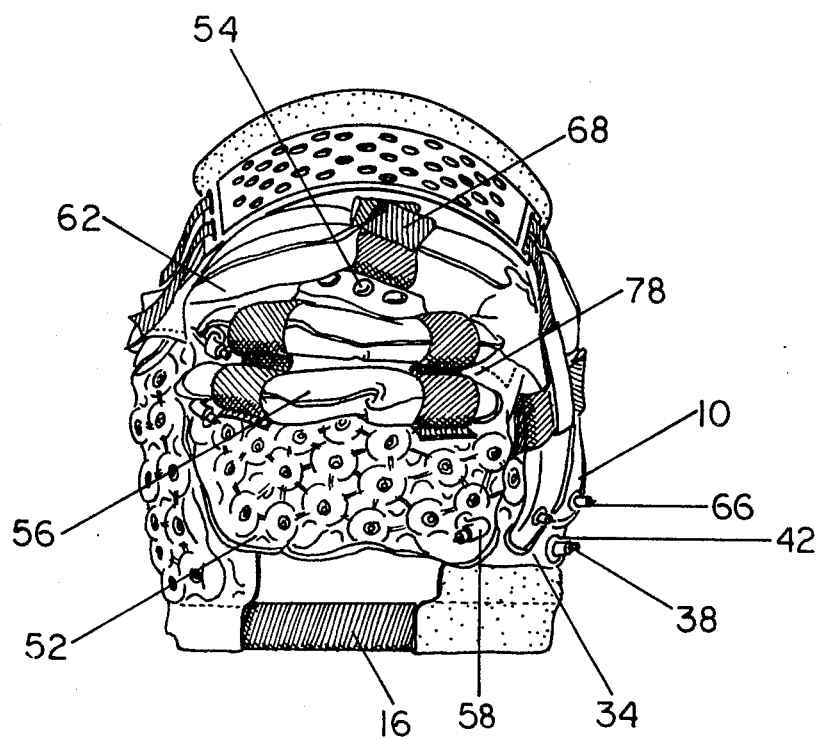
FIG. 5 is a perspective view of the side of the shoulder pads of FIG. 2.

Referring to FIG. 5, pad 14 is provided with a valve 38 which is preferably a check valve, for the purpose of introducing and/or adjusting the amount of pressurized fluid in pad 14. Valve 38 is preferably positioned at a location which does not interfere with the movement of the body and is located outside pad 14 for access without having to remove shoulder pads 10. As will be readily apparent, valve 38 may be positioned anywhere on pad 14 and may extend from pad 14 through any portion of the cushioning region. Valve 38 may have a foam cover to further protect the body where needed.

The valves 38 are provided for inflating the pad 14 to the appropriate internal pressure and for deflating pad 14 when necessary or desirable. Depending upon the individual use, this may take the form of one or more valves secured in the pad at appropriate locations.

The inflation valve 38 for use with the pad 14 provides a very important role. The valve must be lightweight, small in size and capable of withstanding sharp and severe increases in internal pressure without leakage. It should be easy to work with and capable of being located in an area where it will not be subjected to flexing. The valve adapts better to the heat sealing process when it is placed within a suitable plastic tube 42 which tube is then sealed into the periphery 34 of inflatable pad 14. A particularly suitable valve which meets all of these criteria is the 810 series, two piece auto check valve manufactured by Halkey-Roberts Co. of Paramus, New Jersey and described in U.S. Pat. No. 3,831,629. This valve is conveniently used with a hand held, manually-operated pump (not shown) also manufactured by Halkey-Roberts and utilizing the valve shown in U.S. Pat. No. 3,429,338. This pump and valve combination permits the pads 14 of the present invention to be mass produced but then adapted by adjusting the internal air pressure to suit the individual needs of the wearer.

Referring again to FIGS. 3 and 4, preselected regions 36, formed by heat sealing adjacent surfaces of plies 26, 28, are sealed off according to a predetermined design. The heat sealing at 32 around the periphery of pad 14 and at the preselected regions 36 form a quilted configuration. The quilted configuration of pad 14 for shoulder pads 10 is determined at least in part by the end use of the pad 14 and that portion of the body being protected. Such configuration also facilitates the conformation of the undergarment 12 to the contour of the upper torso of the body thereby enhancing the cosmetics of shoulder pads 10. Portions of preselected regions 36 may be enlarged where the pad is particularly susceptible to leakage.

The internal sealing forming preselected regions 36 results in the formation of a plurality of air chambers 44 having fluid communication one with another. Air chambers 44 then function as a pneumatic cushion when pad 14 is pressurized. Air chambers 44 will vary in size in accordance with the build of the wearer. As will be understood, when one or more air chambers 44 are sealed off from the others in the pad thus forming its own inflatable region, a separate valve must be provided.

The unsealed regions between the peripheral sealed regions at 34 and the sealed internal regions 36 create joints or peripheral fluid passageways 45 at the periphery and joints or internal fluid passageways 47 internally of the periphery. Passageways 45, 47 give variable pressure pads 14 a quilted configuration. The lightweight, non-elastic fluid-impervious fabric material, when heat sealed at the periphery and internally of the periphery, creates a crinkling or multiple folds 49 at peripheral passageways 45 and a crinkling or indentations 51 at internal passageways 47. Thus peripheral passageways 45 and internal passageways 47 provide a natural valving or baffling to the flow of fluid between chambers 44. Folds 49 and indentations 51 are formed in the material upon inflation of quilted variable pressure pad 14. Internal passageways 47 are larger in cross-section than peripheral passageways 45 and therefore permit a greater volume of fluid flow upon impact from an external force. Folds 49 include several folds in the material at peripheral passageway 45 and substantially block flow through passageway 45 until an external force is applied. Indentations 47 merely constrict the flow. When an external force is applied, folds 49 and indentations 51 flex or part and open up permitting flow through passageways 45 and permitting greater flow through passageways 47. The momentary blockage or baffling of flow through passageways 45, 47 creates a back pressure build up in chambers 44 preventing a "bottoming out" of quilted variable pressure pads 14. Such natural valving or baffling effect is discussed further hereinafter with respect to tubular variable pressure pads.

Seal regions 36 have the additional function of creating air pockets 46. An air pocket 46, shown in FIG. 4, is created by two adjacent air chambers 44, region 36 between the air chambers, and the body at 53. Perforations 48 are made in regions 36 to allow air flow through undergarment 12. Upon receiving an external force, air pocket 46 is constricted causing air to rush through perforations 48 thereby creating a chimney effect. The chimney effect and perforations 48 permit shoulder pads 10 to breathe so as to provide ventilation to the body. Such ventilation is a necessity to the comfort of the wearer of the uniform. Perforations 48 have a further advantage in that they lighten the weight of the uniform and are used to fasten other cushions to undergarment 12. The perforations 48 may be sealed off using a lining (not shown) where the cooling effect is undesirable such as in cold weather.

Referring now to FIG. 5, to protect the ends of the shoulders, undergarment 12 includes wing pads 52 which may be integral with pads 14 or may be separate pieces appropriately attached to undergarment 12 such as by snaps 54. Wing pads 52 are formed in the same manner and made of the same material as quilted variable pressure pad 14. A valve 58 is included to provide the necessary fluid pressure.

Referring again to FIG. 2, additional cushioning is provided for shoulder pads 10 by air cushions 62 on and around the shoulders of the upper torso due to the intense contact of football players in blocking and tackling using that area of the body. Air cushions 62 each include approximately four self-contained and self-cushioning air tubes 64, the number depending upon the individual player's needs and position. Air tubes 64 are made of the same thin, lightweight, non-elastic, flexible, fluid-impervious woven fabric material as pads 14. A strip of such material is cut to conform to the contour of the shoulders and is rolled into a tube with the mating ends being heat sealed in the same fashion as pads 14. A valve 66, similar to valve 38, is provided in one end of tubes 64 to fill tubes 64 with fluid and is appropriately located to prevent interference with the wearer. Each air tube 64 is individually air inflated, has its own valve 66 and is individually affixed to the undergarment 12 by a plurality of elastic straps 68 which loop over the individual tubes 64 across the shoulder. Straps 68 may be affixed to undergarment 12 by perforations 48. The length of tubes 64 may vary and there is no particular optimum length. Pressure is individually controlled in tubes 64. Air chambers 44 and air cushions 62 may be varied according to athletic position and air cushions 62 may be eliminated under certain circumstances. Comparable air cushions 56 are shown in FIG. 5 attached to wing pads 52.

A shield 72 is disposed over air cushions 62 and is preferably made of a polycarbonate material. The polycarbonate material comes in all thicknesses but preferably is ⅛ inch thick for shield 72. Polycarbonate shield 72 is vacuum formed to conform to the contour of air cushion 62 sized to the shoulder. The polycarbonate material has advantages over a polyethylene material because once it is vacuum formed the polycarbonate holds its shape, is very lightweight and is literally shatterproof. Polyethylene does not have good shatterproof resistance and hardness and therefore poses a hazard to the player. Shield 72 has two elongated slits 74 which receive Velcro tipped straps 76 attached to undergarment 12 by passing through the loops formed by straps 68 for air cushions 62. Shield 72 has ventilation holes 75 to permit the shoulder pads 10 to breathe around the shoulder area. Wing shields 78 shown in FIG. 5 are affixed to wing pads 52 to provide a hard cover for wing pads 52.

Although it is preferred not to cover shield 72 with foam rubber, foam rubber may be used as a cover such as shown on forearm pads 40 in FIG. 8. Under National Football League rules, only hard surfaces worn from the elbows down must be covered with a foam rubber cover. Hard surfaces are preferred on shoulder pads 10 to provide noise upon player contact. As shown in FIG. 2, foam rubber padding 77 is used on the inside edge of shields 72 to protect the neck. The peripheral edge of shield 72 may also be taped such as at 79 to avoid the edges of shield 72 from rubbing against the pads.

Referring now to FIG. 13 there is shown an alternative embodiment of the polycarbonate shield 72. The single piece shield 72 is replaced with a fish scale design shield 232 where a plurality of overlapping rows of egg-shaped polycarbonate discs 234 are attached to a mat 236. The discs 234 each have a pin hole 238 located in the upper portion of their width for attachment to the mat 236 by any suitable means such as thread or string 240. The discs 234 are mounted end for end in making up a row with an overlapping row being mounted on an axis coinciding with the center line of the longitudinal axis of the row to be overlapped. The discs 234 in the overlapping row are mounted to the mat 236 approximately at the point of the mating of the ends of the disc forming the row to be overlapped.

The fish scale shield 232 permits flexibility so that as the body moves, various discs 234 on the shield 232 move instead of a whole sheet of polycarbonate. When a force is placed on the shield 232, it disperses the forces at least as well as the integral single sheet. In some cases the fish shield 232 may give more support because of the overlapping of the discs 234.

Referring again to the preferred embodiment of FIG. 2, shoulder pads 10 are primarily designed for protecting the shoulder area by cushioning and dispersing the blows caused during blocking and tackling. The quilted variable pressure pad 14 is inflated to a pressure of approximately 15 to 16 psi with the air cushion 62 having a pressure of approximately 40 psi to add an additional pneumatic cushion for the shoulder. Shield 72 covers that portion of the shoulder receiving the greatest impact and disperses the force over the air cushion 62 and quilted variable pressure pad 14. The shoulder pads 10 are designed to absorb the impact of two men weighing two hundred and forty pounds running at each other at a speed of fourteen miles per hour. The combination of quilted variable pressure pads 14, air cushion 62 and shield 72 is much flatter than prior art equipment and conforms better to the contour of the body thus achieving cosmetics in smoothness of contour.

In operation the perforated undergarment 12 is air inflated for wide dispersal of the forces. The air cushions 62 have a higher fluid pressure for more direct displacement of energy and shock in specific areas of the body. The polycarbonate shield 72 provides noise level for the game and disperses the shock over the air cushions 62. The air cushions 62 take the shock and disperse it in two directions while the undergarment 12 generally disperses the shock in four directions. The air cushions 62 will be larger in diameter than the air chambers 44 of the pads 14 because the forces it receives are more severe. Quilted variable pressure pads 14, air cushions 62, and shield 72, individually and jointly, apportion the external force over an area greater than the impact area of the external force.

Figure 6:
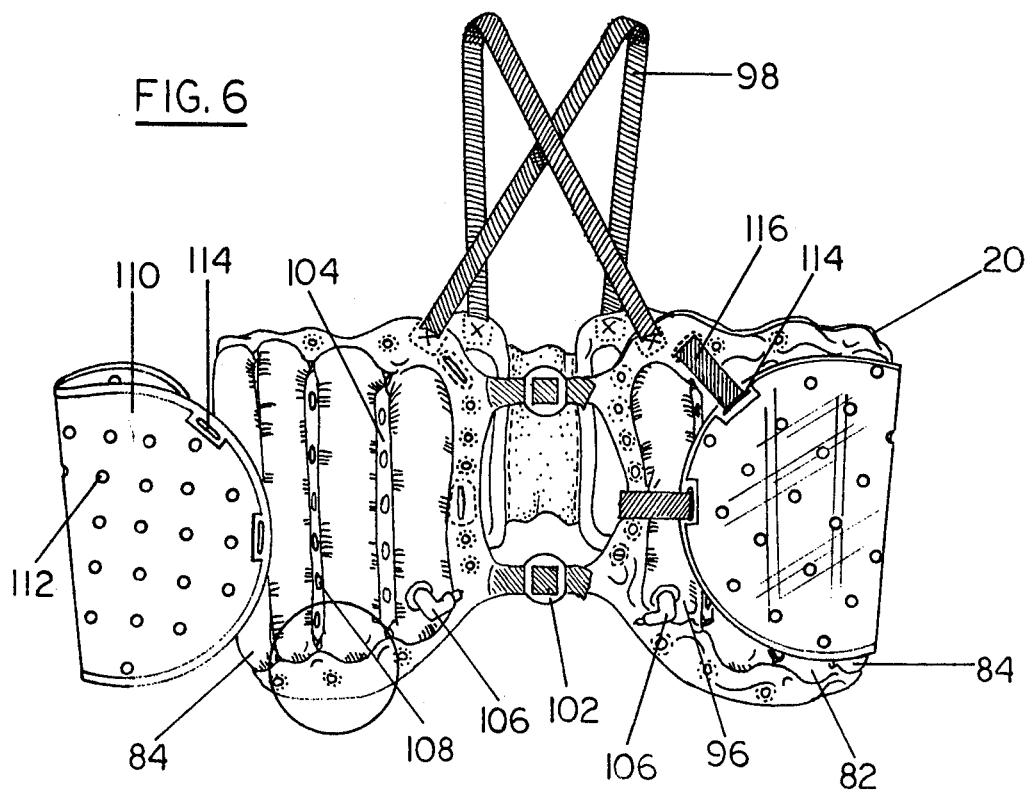
FIG. 6 is a perspective view of the front of the rib pads.

Referring now to FIG. 6, rib pads 20 include an undergarment 82 having two variable pressure pads 84 attached together to form two front portions, two side portions and two back portions. Each variable pressure pad 84 has two separate inflatable sets of air chambers 96. Undergarment 82 has two shoulder straps 98 connected in front and back and extending over the shoulders. The front portions of pads 84 are connected together in front by buckles 102 or by any appropriate fastening means. Flaps may be used between buckles 102 and the body to prevent irritation.

The air chambers 96 of variable pressure pad 84 are formed by heat sealing the adjacent surfaces of the plies of material forming preselected regions 104. Regions 104 distinguish variable pressure pads 84 from pads 14 by forming a tubular configuration rather than a quilted configuration. Tubular pressure pads do not have internal fluid passageways as do the quilted variable pressure pads. Valves 106, the same type as valves 38, are used to inflate the individual chambers. The air pressure for rib pads 20 is approximately 22 to 25 psi.

Variable pressure pads 84 are the same as variable pressure pads 14 except for the air chamber configuration and internal fluid passageways. Pad 84 is constructed of two superimposed piles of thin, lightweight, non-elastic, flexible, fluid-impervious woven fabric material heat sealed around the periphery and at preselected regions 104. The fabric material does not stretch or "balloon" out of shape and is inflated with any suitable fluid. Preselected regions 104 and adjacent air chambers 96 form air pockets with the body comparable to air pockets 46. Perforations 108 are made in regions 104 to allow air flow through rib pads 20 creating a chimney effect upon constricting the air pockets.

Rib pads 20 further include shields 110, preferably of a polycarbonate material, vacuum formed to the contour of the ribs. Shields 110 have ventilation holes 112 to permit pads 20 to breathe about the rib area. Slits 114 are provided in shields 110 for receiving straps 116 affixed to undergarment 82 for mounting shields 110 on undergarment 82. Shields 110 may have a foam rubber cover. The shield 110 is adjustable and is used as a blunting device against exterior blows such as are caused during a football game.

Pockets or envelopes may be provided in undergarment 82 for housing shields 110. Where shields 110 are housed in such pockets or envelopes, the shields will have a foam rubber cover such as those used on forearm pads 40. Permitting shields 110 to be inserted into such pockets permits one to build his own pads and fine tune them to his individuals abilities, activities and movements. For example, the pads may be adjusted to conform to the dexterity of the person i.e. whether he is right handed or left handed. By having the pads very module, the trainers and doctors may vary them and avoid buying a new piece of equipment.

Referring again to FIG. 1, the remainder of the uniform includes bicep pads 30, forearm pads 40, hip pads 50, thigh pads 60, knee pads 70 and shin pads 80. These are preferably constructed of variable pressure pads having a tubular configuration such as pads 84 and are worn by the player utilizing attachment means well known in the art. Details of these pads are disclosed below.

Referring initially to FIG. 7, bicep pads 30 include tubular variable pressure pad 120 secured around the bicep by means of elastic band 122 sewn to pad 120. Bicep pad 30 may be releasably attached to wing pads 52 of shoulder pads 10 by appropriate fastening means such as Velcro. The tubular air chambers 124 of pad 120 are generally vertical and extend around the front, side and back of the arm. Valve 126 permits inflation of pad 120.

Referring now to FIG. 8 illustrating forearm pad 40, tubular variable pressure pad 130 formed by tubular air chambers 132 is affixed to the forearm by means of a plurality of straps 134 and has a valve 136 for inflation. Tubular air chambers 132 extend generally parallel to the axis of the forearm. An individual set of air chambers 132 extend over the back of the hand. A shield 138 is affixed over the upper portion of pad 130 and is covered with a foam rubber 140 by an appropriate adhesive. Form rubber 140 is approximately ⅜ inch thick and is required by the NFL rules.

Referring now to FIG. 9, the hip pads 50 include three tubular variable pressure pads 142, two side portions 144 and a tail bone protector 146. Pads 142 are mounted on an adjustable belt 148 by means of slots 150 in hip pads 50 which receive the belt 148. The tail bone protector 146 is of an abbreviated length. Tubular variable pressure pads 142 are covered by a polycarbonate shield 152. Shield 152 is mounted on pads 142 by an appropriate fastening means.

Referring now to FIG. 10, the thigh pads 60 include tubular variable pressure pads 170 mounted on the thigh by appropriate fastening means such as straps 172. Pads 170 have tubular air chambers 174 which are generally vertical. A polycarbonate shield 176 is formed to the contour of the thigh and includes slots 178 for strapping shield 176 to pads 170. Ventilation holes 180 are provided in shield 176 to permit thigh pads 60 to breathe.

Referring now to FIG. 11, knee pad 70 includes tubular variable pressure pads 190 having air chambers 192 which are generally horizontal. The tubular air chambers 192 are designed to generally conform to the movement of the knee. A void 194 is located in pads 190 over the knee cap. A knee cup 196 is mounted on pad 190 to cover the knee cap. Knee cup 196 has slots 198 for receiving straps 200 for attaching cup 196 to pad 190. Knee pad 70 may be attached to the leg by any appropriate means. An elastic band 202 is shown in FIG. 11 sewn to pads 190. Pads 70 may, however, be strapped to the leg or mounted within envelopes or pockets in the pants of the football uniform.

Referring now to FIG. 12, the shin pads 80 are made of tubular pressure pads 160 having air chambers 162 which are generally vertical. Pads 160 are affixed to the leg by appropriate fastening means such as straps 164 sewn onto pads 160. A shield 166 is mounted on variable pressure pads 160 by appropriate fastening means such as straps 164. Shield 166 has apertures 168 for ventilation.

In order to understand the inventive cushioning of the present invention, reference will now be made to FIGS. 15 and 16 describing the valving of the tubular variable pressure pads such as for example tubular variable pressure pad 84 for the ribs. It should be understood that a description of tubular pressure pads 84 also describes the tubular variable pressure pads on the other pieces of equipment. The unsealed regions between the sealed internal regions 104 and peripheral seal 105 form joint or peripheral fluid passageway 212 located around the periphery of variable pressure pad 84 and provides fluid communication between adjacent tubular air chambers 96A and 96B. The interior sealing 104 which defines air chambers 96 within tubular variable pressure pads 84 does not fully seal off each chamber 96A and 96B to isolate it from the other (although selected chambers may be isolated if desired). The lightweight, non-elastic fluid-impervious fabric material, when heat sealed at the periphery and internally of the periphery, creates a crinkling or multiple folds 210 at peripheral passageways 212. Thus peripheral passageways 212 provide a natural valving or baffling to the flow of fluid between chambers 96A and 96B. Folds 210 are formed in the material upon inflation of tubular variable pressure pad 84. Folds 210 include several folds in the material at peripheral passageway 212 and substantially block flow through passageway 212 until an external force is applied. When an external force is applied, folds 210 flex or part and open up as shown in FIG. 16B permitting flow through passageways 212. The momentary blockage or baffling of flow through passageways 45, 47 creates a back pressure build up in chambers 96 preventing a "bottoming out" of tubular variable pressure pads 84.

The crinkling or folds at the peripheral passageways are formed by a natural lateral shrinkage in the variable pressure pad and results in the pad folding over on itself at points of lesser internal structural support when pressurization occurs. In the design of quilted and tubular variable pressure pads 14 and 84, this creasing or valving will occur at the peripheral passageways 45, 212 communicating between the chambers 44, 96 thereby causing passageways 45, 212 to become more restrictive to the flow of fluid. The sides of the peripheral passageways 45, 212 and the tendency of the walls to constrict around them because of the above-mentioned effect, serve to provide internal valving which aids in minimizing surges of fluid pressure within the variable pressure pads 14, 84 as the external force placed upon it varies.

The crinkling or folds of the variable pressure pads at the peripheral passageways are also caused by the fabric resisting distention and stretching when it is inflated or pressurized. Upon receiving a sharp blow, the peripheral passageways are closed completely for a few milliseconds thereby preventing a "bottoming out" of the fluid chambers. These tend to provide internal valving by changes in orifice size which aids in minimizing the surges of fluid pressure within the variable pressure pads as varying external pressures are placed upon it.

In an athletic event, the actual forces applied to certain portions of the body do not fall in certain areas. By providing for fluid passage from one chamber to another to occur principally around the periphery, additional cushioning is provided. The forces, rather than working against fluid passage between the chambers, cause the fluid to flow naturally to those areas where it is most needed to compress and cushion the impact.

Passageway 212 is sized to restrict fluid flow from one chamber 96 to the other so as to prevent surges of fluid passing between chambers 96A and 96B when forces are applied to the outside surface of the variable pressure pad 84 and to cause a momentary build up of pressure within a chamber when sudden, strong forces are placed on that chamber, thus providing an extra measure of cushioning effect. Pressure build up is much greater at the peripheral passageways in the tubular variable pressure pads than in the quilted variable pressure pads since the quilted variable pressure pads have internal fluid passageways. Thus tubular variable pressure pads can better handle greater external forces than quilted tubular pressure pads.

The valving of the variable pressure pads at the passageways is critical to the present invention since they control the flow of fluid between the fluid chambers in response to external pressure. The valving permits the air to pump back and forth and vary from one chamber to the other. Were the chambers to be sealed, the shock from a blow would merely be transferred from the pad to the body. Valveless pneumatic devices have not been used in the past because they do not permit pressure variation. The passageways are adapted by size and shape to restrict the air flow between the chambers in accordance with a positive, functional plan.

The size, location and pattern of the fluid passageways are combined with the number, size, shape and pattern of the fluid chambers to produce an appropriate fluid communication and restrictive flow pattern to maximize the effectiveness of each of the variable pressure pads for their particular location on the body. In cooperative combination with the flexible, adaptive sealing technique and the resistance of the fabric to deformation under pressure, the fluid passageways of the invention may be adapted to restrict air flow according to a particular plan. It can be seen that the pattern of interior sealing may be adapted to provide for a wide variety of internal fluid flow patterns. To take into account the varying forces placed upon a pad of the present invention as the pad is worn during an athletic event, it will be preferred to locate and size the passageways to restrict flow generally from one preferred location to another. At the same time, fluid communications between chambers should be adapted, in combination with chamber size and shape, to maximize the flow of fluid from all chambers in preferred directions.

Referring now to FIGS. 13 and 14 in a variation to the standard design of the variable pressure pads for the uniform, the pads of the present invention may be adapted for certain body anomalies which call for little or no pressure at particular locations of the body. FIG. 13 shows the shoulder pads with an undergarment having tubular pressure pads 220. The sealed preselected regions 222 define one or more fluid-containing chambers 224 within the pad 220 which extend over the shoulders. To permit chambers 224 to conform to the contour of the shoulders, chambers 224 are made into a series of successive, short tubular chambers by regions 222 whereby the variable pressure pad 220 can bend with the body contour over the shoulders.

Preselected regions 222 also define entire separate areas of the overall surface of the pad 220 which do not contain any fluid whatsoever. When the pad is inflated, these areas tend to be recessed and shall be referred to herein as "voids" 226. Referring to FIG. 14, these void areas 226 are totally surrounded by pneumatic cushions 224. The shield 230 is placed over the top of the adjacent cushions 224 to create a bridging effect over the void 226 whereby as pressure is placed on shield 230, the forces are transferred to the surrounding air chambers 224 and not to the area covered by the void 226. Voids are used where one does not want any pressure on an injured part of the body making voids particularly valuable in the treatment of certain portions of the body by isolating such portions by predetermined design from pressure and/or chafing in order to promote healing or otherwise correct an improper body condition.

Thus, during the heat sealing process, voids may be particularized, adapted and produced to suit the individual needs of the wearer. Any number of patterns may be conceived by which the internal regions of the pads are sealed off to form on the one hand voids and on the other hand the internally communicating chambers which provide for the pneumatic cushioning. In the case of football uniforms, voids are used at body locations where the wearer does not wish any pressure especially where the body has been injured in that location. A void will cover the portion of the injury and will have an air inflated cushion around the area.

It will become apparent to those skilled in the art that many different design patterns may be utilized, combining the size, location and pattern of the peripheral fluid passageways with the number, size, shape and pattern of the air chambers. For example, an extra large fluid chamber may be provided in one of the rib pads to take into account the stronger forces exerted on one side of a right handed player during a football game. A side chamber may be totally sealed off from the rest of the pad by enlarging an internal sealed region or extending an internal sealed region during the heat sealing process to meet a peripheral sealed region thereby preventing communication of one chamber with the other chambers of the pad. In other designs a larger fluid chamber may be proposed with an additional inflation means or valve to provide for inflation of particular regions. As will be observed, the pattern of sealing the internal regions within the periphery of the pad may be adapted in a variety of ways to provide fluid flow patterns suitable for particular end uses. Different athletic events will require different uses and will obviously command different restricted flow patterns. The devices of the present invention may be readily adapted to meet these needs.

The preselected internal sealed regions such as 36 and 104 do not provide any cushioning. By preselecting the design pattern, size and shape of these regions which are created during the sealing process, they are able to be used in conjunction with the cushioning portions made by the fluid chambers of the pads to provide very valuable features. Obviously the primary function of the regions is to define the boundaries and shape of the fluid chambers and as such, the width of those regions as opposed to the length may be no more than is necessary to insure adequate seal under the pressures to be accommodated. Preliminary studies indicate that a minimum of approximately 20% of the total surface area of the variable pressure pads should be taken up with these heat sealed regions. In other words, the purpose of the region is not simply to delineate and separate the fluid chambers, but rather the regions are to be considered an integral aspect of the design of the pads of the present invention. In combination with the pneumatic cushions, the region areas contribute to the total cushioning effect of the pads of the invention. The size, shape and number of these regions should be taken into account equally along with the size, shape and number of the fluid cushions and the size and shape of the fluid communication passageways in creating an overall pattern of fluid flow and internal pressure necessary to provide for an effective pad.

The various variable pressure pads utilize to the fullest extent, the self-contained and self-cushioning nature of the present invention. The pads may be impregnated with elastomeric material to increase this wear characteristic. The use of fasteners, such as by means of opposing strips of Velcro material, is desirable since it permits anyone to remove and replace any one of the variable pressure pads. Where the composite structure of the undergarment, air cushioning and shield are used, they are maintained on the body by means of any suitable arrangement such as straps and secured to the outer surface of the upper layer. As an alternative to having the layers readily removable from each other and inflatable at will, the entire composite may be formed by placing the layers on top of each other in an appropriate fashion, inflating the device, and then heat sealing the three parts together around the periphery. The pads of the present invention weigh approximately four pounds as compared to a weight of approximately 22 to 26 pounds for prior art equipment.

In operation, the present invention is uniquely adapted to respond to forces applied to the body during athletic events. Accordingly, when the invention is worn and the wearer contacts an external force, the flexible, cushioning nature of the invention responds accordingly to such forces. In the "strike" phase the force is borne by a certain portion of the invention which may comprise a cushion of fluid chambers or a pneumatic "pillow". The force of the "strike" will tend to force air from the chambers making up the pillow into adjacent chambers. However, because of the restricted passageways between communicating chambers, a back pressure will build up in the strike chamber and in its adjacent chambers receiving the force, producing a momentary additional resistance to the force, and as a result, an additional cushioning effect. Similarly, due to the flexible nature of the pad itself, the joints between the chambers will tend to flex thereby providing an additional momentary restriction to the fluid passageways. This flexing action will continue as other forces are applied to other portions of the body, thus, a series of restrictions is produced, forming a valving or baffling action which tends to restrict the movement of the fluid from chamber to chamber and provides additional pressure where it is most needed, that is, in the chambers receiving the strike force.

In the event pressure is angularly exerted on the pad as during certain maneuvers which are experienced on the football field, this valving or baffling effect will restrict the fluid flow in a lateral direction. The fluid will be forced from that portion of the pad underlying the angular force to that portion of the pad underlying the outside area around the force, but at a restricted flow. Thus, that porton of the pad under the angular force will continue to provide an additional protective cushion. In all events, the restricted valving function of the fluid passageways acts to assure that those portions of the pad receiving the additional external pressure will not be so compressed as to "bottom out". In other words, the wearer will always have all portions of his body supported on a cushion of fluid during any of the varied maneuvers involved during the wearing of the uniform.

The pesent invention provides a cushioning response which is extraordinary in relation to its size and weight. It not only absorbs the energy of the force that is placed on it but returns most of the energy in these forces in an apportioned or distributed fashion thereby providing significant cushioning to the wearer. The pad may also be utilized as a cushion for only selected portions of the body in which case it may be secured by any suitable means. It is an important feature of the invention that the pad is self-contained; that it need not be supported or contained within a specially constructed region of the uniform in order to be fully functional. Thus it may be made to be easily removeable and replaceable. It may also be utilized by itself with nothing more attached to the pad than that necessary to keep it on the body and protect it from excessive wear. Further the uniform is washable after every game making it very hygienic and if it is damaged, the uniform can be repaired by gluing a patch over the hole using some urethane glue.

Another advantage of the invention is its improved silhouette and cosmetics. The flexibility of the invention permits it to be attached close to the body so that the uniform conforms to the body shape. The uniform is very flat through the use of smaller fluid chambers and higher inflation pressures. Body shape is a major determination in the direction of the fluid chambers forming the variable pressure pads since it is not necessary that the fluid chambers be in a particular direction. The fluid chambers may vary with the position of the players when a lineman may have a pad with larger fluid chambers. These features prevent the uniform from riding high on the body and yet still provide absorption of all the impact.

Other advantages of the invention are that it permits great mobility, is lightweight, hygienic, easily stored, and easily maintained. The uniform can be reduced in size by vacuuming out the air and can be carried in a six-inch diameter bag. The invention is a "build-it-yourself" protective device that enables great mobility for the player and directional use for the trainer and doctor. Prior art devices "bottom out", leak, cannot change the inflation, and are elastic type tubes. Further, the invention may be adapted to conform to the various characteristics of each individual.

Figure 17:
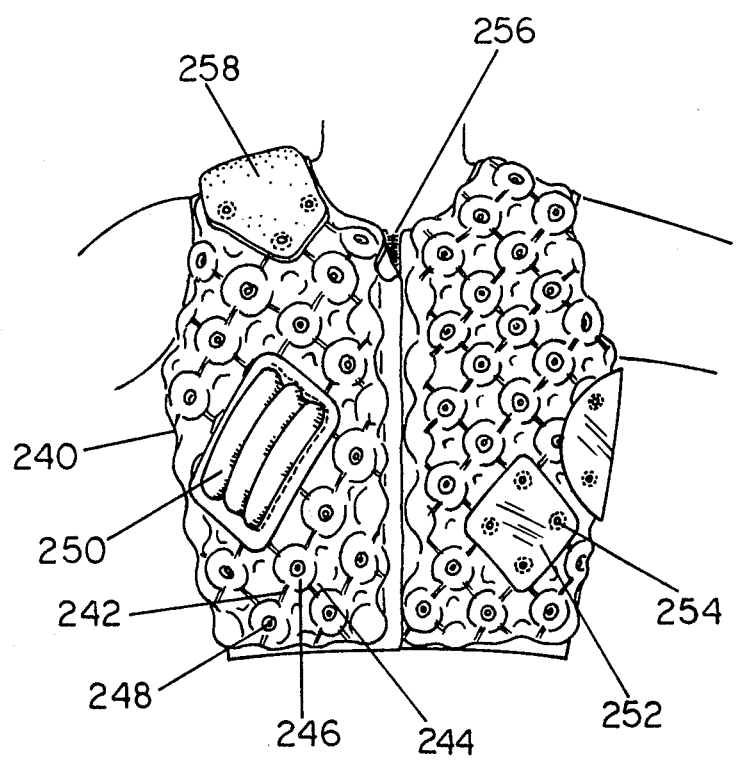
FIG. 17 is an elevation view of a protective vest.

Referring now to FIG. 17, there is illustrated a "build-it-yourself" protective undergarmet or vest 240. Protective vest 240 includes variable pressure pad 242 with a quilted configuration. It is, of course, understood that a tubular configuration may be used especially where vest 240 is expected to encounter large external forces. Fluid chambers 244 are formed by preselected regions 246. Regions 246 have perforations 248 permitting the vest 240 to be ventilated and to breathe. Perforations 248 are used to attach additional cushioning devices such as air cushion 250, shield 252, and foam rubber pad 258. Snap-on buttons 254, attached to air cushions 250 and shield 252, extend through perforations 248 for engagement with another portion of button 254 thereby capturing a portion of region 246 therebetween to secure the protective device onto vest 240. Thus the wearer may adapt his vest to suit his individual tastes and needs by selecting particular protective devices and locating them anywhere needed on vest 240. The protective devices may take any shape as for example rectangular, circular, square, etc. and may be made of a variety of materials such as foam rubber, pneumatic pad, polycarbonate shield, etc. Vest 240 can be worn as clothing and fastened using a zipper 256 or other similar fastening device. It should also be understood that a complete suit covering the entire body may be made of variable pressure pads to protect and/or insulate the whole body.

The device of the present invention finds particular utility in several other areas. In the field of athletics or sports, the emphasis is on strength and effectiveness combined with light weight. Different demands are placed on the device depending upon the sports in which it is to be used. Nevertheless, each of those endeavors requires a lightweight garmet. Even the lightest weight results in a burden during any extended playing endeavor. The device of the present invention weighs approximately 4 pounds and has a strength and structural integrity factor equal to the strongest cushioning devices now being used.

In the field of military use, while weight remains important, its importance is secondary to the ability of the device to provide long lasting, effective cushioning. The device of the present invention is extremely resistant to puncture, is convenient to inflate and deflate to the desired pressure at any time, and is able to withstand extended periods of flexing and rubbing without a noticeable effect on the structural integrity.

In the medical field, the device finds particular utility in that it may be adapted to suit the individual needs of the patient, both by adjusting the internal pressure to increase or decrease cushioning at certain areas and also, by predetermined design, to eliminate whole regions where any contact at all is made with the body. Because the device is constructed of a non-elastic material, which does not distend when subjected to increases and internal pressure, the surface area and structure of the device may be precisely designed according to predetermined functional intent. The device is also capable of being fitted precisely to any size and shape of the body, and it will maintain that shape and size.

The invention can be used for insulation in clothing, as for example, a ski jacket. Air holes and a gortex outer covering for waterproofing are provided in the clothing. Gortex permits no water to go in but allows air and vapors to go out. One can also vary the inflation to vary the amount of insulation.

The invention may be used for padding on dashboards in cars and will reduce the weight of a car.

The present invention has been described in detail with respect to preferred embodiments thereof as required by the patent laws. However, it should be understood that modifications and changes to various aspects of the embodiments and alternatives shown and described may be made while still coming within the spirit and scope of the invention. For example, although the preferred method and making the device of the present invention has been disclosed as superimposing two plies of impregnated, non-elastic fabric, it should be apparent that a single ply, suitably impregnated, may be used, in which case the single piece of fabric is simply folded over on itself and appropriately sealed. In addition, while emphasis has been placed on the construction to be utilized solely for cushioning certain parts of the body, the invention may also be embodied in a construction adapted to cushion other items. Indeed, with appropriate fabrication design and techniques, the invention may be used on padded devices for automobiles. Many different combinations of the different variable parameters, such as the cooperative placement of voids and pneumatic cushions, which are involved in construction of the device of the present invention, will be apparent to those skilled in this art.

Changes and modifications may be made in the specific illustrated embodiments of the invention shown and/or described herein without departing from the scope of the invention as defined in the appended claims.

I claim:

1. Rib pads for protecting the ribs comprising:
    a fluid pressurized pad covering the ribs and being made of a fabric material which does not distend under pressure, said pad including a plurality of interconnected fluid chambers formed by sealing adjacent surfaces of said material;
    valving means for preventing surges of fluid within said fluid chambers, said valving means including folds of said material at the interconnections of said fluid chambers whereby said folds must be opened to permit fluid flow from one chamber to another; and
    rigid means for apportioning an external force applied to said pad, said rigid means covering the exterior of said fluid pressurized pad.

2. The rib pads of claim 1 further including vent means for providing air flow through said sealed surfaces;
    said pad being adjacent the wearer's ribs whereby upon impact, a chimney effect is caused beneath said fluid pressurized pad to cool the wearer's skin.

3. The rib pads according to claim 1 wherein
    said fluid chambers are formed by two superimposed plies of a lightweight, non-elastic fluid-impervious fabric material having adjacent surfaces sealed around the periphery thereof and at regions internally of said periphery thereby defining said plurality of fluid chambers; and
    said folds including crinkles in said material at preselected locations to provide a valving effect causing a back-pressure build-up.

4. The rib pads of claim 3 further including air passage means through said internal regions and rigid means for permitting the flow of air from the wearer's body to the exterior of said rigid means.

5. The rib pads of claim 1 further including fluid passages at the periphery of said pad connecting adjacent fluid chambers, said material forming said fluid passageways folding over and crinkling to constrict fluid flow between adjacent fluid chambers.

6. The rib pads according to claim 1 wherein said rigid means includes a rigid shield to spread the external force over a wide area.

7. The rib pads according to claim 1 wherein said rigid means has vent holes for air passage.

8. The rib pads according to claim 1 wherein said rigid means has a resilient cover.

9. The rib pads according to claim 1 wherein said fluid chambers form a quilted configuration.

10. The rib pads of claim 9 wherein said folds are located on a straight line connecting the centers of said internal regions and by folds in said fluid chambers located around the periphery.

11. The rib pads according to claim 1 wherein said fluid chambers form a tubular configuration.

12. The rib pads of claim 11 wherein said fluid chambers include fluid passageways at the periphery connecting adjacent tubular fluid chambers, said folds forming crinkles in said material at said fluid passageways.

13. The rib pads according to claim 6 wherein said shield has a protective covering on its periphery.

14. The rib pads according to claim 6 wherein said rigid shield includes a polycarbonate shield molded to conform to the contour of the body.

15. A protective rib pad for protecting the ribs comprising:
    two superimposed plies of a lightweight, non-elastic fluid-impervious material forming a pressure tight inflatable pad which does not distend, the adjacent surface of said material being sealed around the periphery thereof and at regions internally of said periphery to form a plurality of fluid chambers and internal and peripheral flow passages, said flow passages having a cross sectional area smaller than said fluid chambers; and
    folds of said material being located at said flow passages to baffle flow between said fluid chambers, the folds at said peripheral fluid passages substantially blocking flow therethrough until an external force is applied to said pad flexing said peripheral folds apart to permit flow through said peripheral fluid passages; said folds at said flow passages permitting pressure equalization between adjacent fluid chambers and providing a baffling effect preventing sudden surges of fluid flow from one fluid chamber to another upon the impact of sudden forces placed on said fluid chambers.

16. The protective pad of claim 15 wherein said fluid chambers and flow passages form a quilted configuration.

17. The protective pad of claim 15 wherein the folds at said internal flow passages create indentations constricting flow therethrough.

18. The rib pad of claim 15 further including at least one perforation in said regions.

19. The rib pad of claim 15 further including means disposed at a predetermined location on said pad for introducing pressurized fluid therethrough.

20. The rib pad of claim 19 wherein said means for introducing pressurized fluid in said pad are positioned within a plastic tube, which tube is then sealed into the periphery of said pad.

21. The rib pad of claim 15 wherein the fabric material is made from woven aramid fiber and coated on at least one side with a fluid-impervious thickness of heat-sealable thermoplastic elastomeric materials, such as polyurethene.

22. The rib pad of claim 21 wherein the adjacent coated surfaces of the fabric are heat-sealed to each other.

23. The rib pad of claim 15 wherein said regions defining said fluid chambers define a void area which contributes to the total cushioning effect of said pad.

24. The rib pad of claim 23 wherein said regions defining said fluid chambers define at least 20 percent of the total surface of said pad.

25. The rib pad of claim 23 wherein said regions include at least one large isolated region where a certain portion of the ribs are isolated from pressure.

26. The rib pad of claim 15 wherein the flexibility of said pad is sufficient to cause said regions to act as joints, folding over and restricting fluid communication from one internal chamber to another as pressure is applied to preselected areas of said pad.

27. The rib pad of claim 15 wherein adjacent fluid chambers form an air pocket against the wearer's body whereby upon receiving an external force, said air pocket constricts causing ventilation.

28. The rib pad of claim 15 wherein said folds are formed by the lateral shrinkage in said material at points of lesser internal structural support.

29. The rib pad of claim 15 wherein said folds are formed by said material resisting distention and stretching when pressurized.

30. A rib pad for protecting the ribs during sports activities comprising:
an undergarment including a pressure tight pad adapted to contain a pressurized fluid without distending or otherwise losing its shape when pressurized and subjected to external forces;
said pad being further characterized in that the walls thereof are thin, non-elastic and flexible, and at least the inner surfaces thereof are coated with a fluid-impervious thickness of heat-sealable material;
a plurality of void, non-pressurizable regions within said pad sealing together the upper and lower walls of said pad in a predetermined pattern and disposed generally perpendicular to the transverse axis of the pad, said void regions comprising at least 20 percent of the total surface of the pad which is exposed to the ribs;
a plurality of internal pressurizable chambers within said pad, defined by the pattern of said void regions, at least some of which chambers are fluidly communicable with adjacent chambers;
fluid passageways located around the periphery of said pad to permit pressurized fluid flow between at least some chambers and defined between the outer walls of the pad and the internal sealed-off regions of the pad, said passageways being sized appropriately such that the fluid flow from one chamber is restricted, when the pad is pressurized, as a result of the flexible walls of the pad folding over themselves at the fluid passageways.

31. The rib pad of claim 30 and including rigid bridge means extending over at least one of said void regions for transferring the impact of an external force to fluid chambers surrounding said one of said void regions.

32. The rib pad of claim 31 and including means for selectively attaching said bridge means to said material.

* * * * *